United States Patent [19]

Wrobel et al.

[11] Patent Number: 4,906,766

[45] Date of Patent: Mar. 6, 1990

[54] N-(6-METHOXY-5-(TRIFLUOROMETHYL)-1-NAPHTHALENYL)-SUBSTITUTED IMINO)METHYL)-N-METHYLGLYCINES

[75] Inventors: Jay E. Wrobel, Lawrenceville; Kazimir Sestanj, Monmouth Junction, both of N.J.

[73] Assignee: American Home Products Corporation, New York, N.Y.

[21] Appl. No.: 325,609

[22] Filed: Mar. 20, 1989

Related U.S. Application Data

[62] Division of Ser. No. 137,381, Dec. 23, 1987, Pat. No. 4,853,412.

[51] Int. Cl.$^4$ .............................................. C07C 143/80
[52] U.S. Cl. .................................. 558//390; 562/427; 560/10
[58] Field of Search .................. 558/390; 562/427; 560/10

[56] References Cited

U.S. PATENT DOCUMENTS

| | | |
|---|---|---|
| 4,391,816 | 7/1983 | Sestanj et al. ........................ 424/274 |
| 4,391,825 | 7/1983 | Bellini et al. ........................ 424/319 |
| 4,439,617 | 3/1984 | Sestanj et al. ........................ 560/39 |
| 4,568,693 | 2/1986 | Sestanj et al. ........................ 514/524 |
| 4,734,435 | 3/1988 | Ferdinandi et al. ................. 514/562 |

*Primary Examiner*—Bruce Gray
*Attorney, Agent, or Firm*—Walter Patton

[57] ABSTRACT

Disclosed herein are N-[[6-methoxy-5-(trifluoromethyl)-1-naphthalenyl][substituted imino]methyl]-N-methylglycines and methods for their preparation. The N-methylglycines are new aldose reductase inhibitors useful for the treatment or prevention of diabetic complications.

1 Claim, No Drawings

N-(6-METHOXY-5-(TRIFLUOROMETHYL)-1-NAPHTHALENYL)-SUBSTITUTED IMINO)METHYL)-N-METHYLGLYCINES

This is a divisional of co-pending application Ser. No. 137,381 filed on Dec. 23, 1987, now U.S. Pat. No. 4,853,412.

BACKGROUND OF THE INVENTION

This invention relates to N-[[6-methoxy-5-(trifluoromethyl)-1-naphthalenyl][substituted imino]methyl]-N-methylglycines, to the processes for their preparation, to methods for using the compounds, and to pharmaceutical preparations thereof. The compounds have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn resulted from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators, see J. H. Kinoshita et al, Biochem. Biophys. Acta, 158,472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesireable accumulation of sorbitol has been demonstrated in the lens, peripheral nervous cord and kidney of diabetic animals, see A. Pirie and R. van Heyningen, Exp. Eye Res., 3,124 (1964); L. T. Chylack and J. H. Kinoshita, Invest. Ophthal., 8,401 (1969) and J. D. Ward and R. W. R. Baker, Diabetol., 6,531 (1970).

N-Naphthoylglycine derivatives of K. Sestanj, et al, U.S. Pat. No. 4,568,693, Feb. 4, 1986, have been reported to be effective inhibitors of aldose reductase.

The present application discloses the novel N-[[6-methoxy-5-(trifluoromethyl)-1-naphthalenyl][substituted imino]methol]-N-methylglycines represented by formula (I), which are effective inhibitors of aldose reductase. They are structurally different from the above noted aldose reductase inhibitors. The closest of the previously reported compounds is seen in U.S. Pat. No. 4,568,693 (Example 52). The present compounds differ by the replacement of a thiocarbonyl (C=S) with a substituted imine (C=N—R). Accordingly, these compounds represent an important new approach to the treatment of diabetes mellitus. The replacement of a C=S by a C=N—R in other cases is disclosed by R. Ganellin, J. Med. Chem., 24, 913, 1981; and D. E. Beattie et al, J. Med. Chem., 20, 718, 1977.

SUMMARY OF THE INVENTION

The N-[[6-methoxy-5-(trifluoromethyl)-1-naphthalenyl][substituted imino]-methyl]-N-methylglycines of this invention are represented by formula (I)

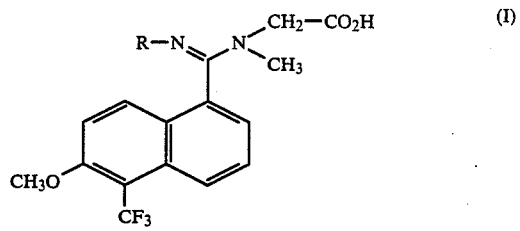

wherein R is —CN, —SO$_2$CR$_3$, or —SO$_{2p}$—BrC$_6$H$_4$ and the pharmaceutically acceptable salts thereof.

The N-[[6-methoxy-5-(trifluoromethyl)-1-naphthalenyl][substituted imino]-methyl]-N-methylglycines can be prepared by the processes described hereinafter.

A method is provided for preventing or relieving diabetes mellitus associated complications in a diabetic mammal by administering to said mammal a prophylactic or alleviating amount of a compound of formulas (I). Such complications include neuropathy, nephropathy, retinopathy and cataracts.

The compounds of formulas (I), when admixed with a pharmaceutically acceptable carrier, form a pharmaceutical composition which can be used according to the preceding method.

DETAILED DESCRIPTION OF THE INVENTION

The compounds of this invention, represented by formulas (I), can exist in rotameric forms. More explicitly, mesomerism imparts a partial double bond character to the carbon-disubstituted nitrogen bond of the amidine group and to the imino nitrogen-nitrile carbon bond when R= —CN and to the imino nitrogen-sulfonyl sulfur bond when R= —SO$_2$CF$_3$ or —SO$_2$-p—BrC$_6$H$_4$. These partial double bond characters lead to restricted rotation about these bonds giving rise to cis and trans rotamers, the restricted rotation being augmented by the bulkiness of neighboring groups. The rotameric forms are included within the scope of this invention. For brevity, the compounds of this invention, including their rotameric forms, are referred to herein as compounds of formula (I).

The compounds of formula (I) form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyl-triethanol and trimethyl-monoethanol) and cyclic ammonium salts, for example the N-methylpyridinium, N-methyl-N-(2-hydroxyethyl)-morpholinium, N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula (I) is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

The N-[[6-methoxy-5-(trifluoromethyl)-1-naphthalenyl][substituted imino]-methyl]-N-methylglycines of this invention may be administered to mammals, for example, man, monkeys or dogs, either alone or in dosage forms, i.e., capsules or tablets, combines with pharmacologically acceptable excipients.

Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the N-[[6-methoxy-5-(trifluoromethyl)-1-naphthalenyl]-[substituted imino]methyl]-N-methylglycines will vary with the form of administration. Furthermore, it will vary with the particular host under treatment. Generally, treatment is initiated with small dosages substantially less than the optimal dose of the compound. In general, the compounds of this invention are most desirably administered at a concentration level that will generally afford effective results without causing any harmful or deleterious side effects. For topical administration, a 0.05–1.8% solution may be administered dropwise in the eye. The frequency of instillation varies with the subject under treatment from a drop every two or three days to once daily. For oral or parenteral administration a preferred level of dosage ranges from about 0.5 mg to about 1000 mg per kilo of body weight per day, although aforementioned variations will occur. However, a dosage level that is in the range of from about 5.0 mg to about 60 mg per kilo of body weight per day is most satisfactory.

Unit dosage forms such as capsules, tablets, pills and the like may contain from about 25 mg to about 1250 mg of the active ingredients of this invention with a pharmaceutical carrier. Thus, for oral administration, capsules can contain from between about 25 mg to about 1250 mg of the active ingredients of this invention with or without a pharmaceutical diluent. Tablets, either effervescent or noneffervescent, can contain between about 25 to 1250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents for example, magnesium stearate.

The N-[[6-methoxy-5-(trifluoromethyl)-1-naphthalenyl][substituted imino]-methyl]-N-methylglycines can also be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 36 ed., Medical Economics Co., Oradell, N.J. U.S.A., 1982. When used in combination, the N-[[6-methoxy-5-(trifluoromethyl)-1-naphthalenyl][substituted imino]-methyl]-N-methylglycines are administered as described previously. The N-[[6-methoxy-5-(trifluoromethyl)-1-naphthalenyl][substituted imino]methyl]-N-methylglycines can be administered with the oral hypoglycemic agent in the form of a pharmaceutical composition comprising effective amounts of each agent.

The aldose reductase inhibiting property of the compounds of this invention and the utilization of the compounds in preventing, diminishing and alleviating diabetic complications by lowering polyols accumulation are demonstrable in experiments using galactosemic rats, see Dvornik et al, Science, 182, 1146 (1973). Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent Laboratory Chow, Purina) and glucose at 20% (w/w %) concentration. The untreated galactosemic group and the drug-treated groups were fed a similar diet in which galactose is substituted for glucose. The test compound was either admixed to the diet or administered by gavage. In experiments involving compound administration in the diet, the average dose administered was calculated from the actual food intake of the animals in each group. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues when frozen can be kept up to two weeks before being analyzed for galactitol.

(c) The polyol determination was performed by a modification of the procedure of M. Kraml and L. Cosyns, Clin. Biochem., 2,373 (1969). Only two minor reagent changes were made: (a) The rinsing mixture was an aqueous 5% (w/v) trichloroacetic acid solution and (b) the stock solution was prepared by dissolving 25 mg of dulcitol in 100 mL of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.] The aldose reductase inhibiting effects of the compounds of formula (I) were also tested by employing an in vitro testing procedure similar to that described by S. Hayman and J. H. Kinoshita, J. Biol. Chem., 240, 877 (1965). In the present case the procedure of Hayman and Kinoshita was modified in that the final chromatography step was omitted in the preparation of the enzyme from bovine lens.

The following tabulated results show that the N-[[6-methoxy-5-(trifluoromethyl)-1-naphthalenyl][substituted imino]methyl]-N-methylglycines of this invention show the property that they diminish the accumulation of galactitol in the lenses and sciatic nerves of rats fed galactose. The figures under L and N represent the percentage decrease of galactitol accumulation in the tissues of the lens and sciatic nerve, respectively, for treated rats as compared to untreated rats.

Examination of the results tabulated below show that the N-[[6-methoxy-5-(trifluoromethyl)-1-naphthalenyl]-[substituted imino]methyl]-N-methylglycines of this invention are well suited as aldose reductase inhibitors and they lower polyol accumulation in tissues of diabetic or galactosemic rats. For example, N-[(cyanoimino)[6-methoxy-5-(trifluoromethyl)-1-naphthalenyl]methyl]-N-methylglycine at a dose of 100 mg/kg/day gave comparable results to N-[[6-methoxy-5-(trifluoromethyl)-1-naphthalenyl]thioxomethyl]-N-methylglycine at 6.4 mg/kg/day. The latter compound is also known as tolrestat.

| Test compound | % inhibition in vitro $10^{-7}M$ | mg/kg/day p.o. | % lowering dulcitol accumulation in vivo | |
|---|---|---|---|---|
| | | | L | N |
| N—[(cyanoimino)[6-methoxy-5-(trifluoromethyl)-1-naphthalenyl]-methyl]-N—methylglycine | 80 | 100 | 0 | 61 |
| | | 26 | 0 | 30 |
| N—[[6-methoxy-5-(trifluoromethyl)-1-naphthalenyl][[(trifluoromethyl)-sulfonyl]imino]methyl]-N—methylglycine | 69 | 56 | 0 | 0 |
| N—[[[(4-bromophenyl)sulfonyl]-imino][6-methoxy-5-(trifluoromethyl)-1-naphthalenyl]methyl]-N—methylglycine | 5 | 55 | 0 | 0 |
| N—[[6-methoxy-5-(trifluoromethyl)-1-naphthalenyl]thioxomethyl]-N—methylglycine(tolrestat) | 65 | 6.4 | 0 | 50 |

THE PROCESS

The [[6-methoxy-5-(trifluoromethyl)-1-naphthalenyl][substituted imino]-methyl]-N-methylglycines can be prepared by the following reaction scheme wherein R is defined hereinbefore and $CO_2R^1$ is an ester group which may be, for example, a lower alkyl, or Ar(lower)alkyl ester, i.e., $R^1$ is lower alkyl or Ar(lower)alkyl.

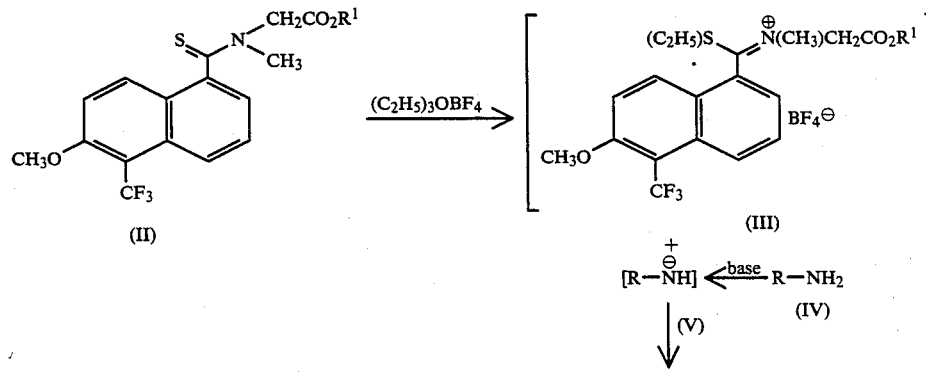

(I) ⟵ hydrolysis 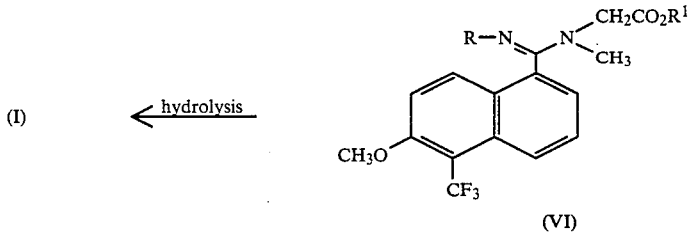

(VI)

More specifically, a process for preparing the compounds of formula (I) comprises:

(a) reacting a thioamido ester of formula (II) wherein $R^1$ is lower alkyl or Ar(lower)alkyl with triethyloxonium tetrafluoroborate to give the corresponding ethylthioimidate tetrafluoroborate salt of formula (III) wherein $R^1$ is defined as above. It is noted that the salt of formula (III) is not isolated in this process; or (b) reacting an amide of formula (IV) wherein R is —CN, —SO$_2$CF$_3$, or —SO$_{2p}$—BrC$_6$H$_4$ with a base to give the corresponding amide anion of formula (V) wherein R is defined as above. It is noted that the compound of the formula (V) is not isolated in this process; or (c) reacting the salt of formula (III) wherein $R^1$ is defined herein with the amide anion of formula (V) wherein R is defined herein to give the corresponding amidine ester of formula (VI) wherein R and $R^1$ are defined herein; or (d) hydrolyzing the amidine ester of formula (VI) wherein R and $R^1$ are defined herein to obtain the corresponding compound of formula (I) wherein R is defined herein.

More specifically the thioamide ester of formula (II) is reacted under anhydrous conditions with about one to two molar equivalents of triethyloxonium tetrafluoroborate in an inert solvent, e.g. dichloromethane or 1,2-dichloroethane to obtain the compound of formula (III). The reaction is performed conveniently at temperatures ranging from 20° C. to about 70° C. and at times ranging from one to four days.

The amide of formula (IV) is then reacted with a base to obtain the amide anion of formula (V). The reaction is most conveniently performed using one to ten molar equivalents of sodium hydroxide, potassium hydroxide, sodium bicarbonate, or potassium carbonate in an aqueous lower alcohol solvent. The reaction is performed conveniently at temperatures ranging from 0° C. to 30° C. and at times ranging from 1 minute to 15 minutes. Alternatively, the reaction can be performed under anhydrous conditions using one to two molar equivalents of a sodium or potassium lower alkoxide, such as potassium t-butoxide in an anhydrous lower alcohol solvent such as ethanol. The reaction is performed conveniently at temperatures ranging from 0° C. to 30° C. and at times ranging from 1 minute to 15 minutes.

The ethylthioimidate tetrafluoroborate salt of formula (III) is then reacted with one to four molar equivalents of amide anion of formula (V) to obtain the amidine ester of formula (VI). The reaction is most conveniently performed in an aqueous lower alcohol solvent or an anhydrous lower alcohol solvent such as ethanol. The reaction is performed conveniently at temperatures ranging from 0° C. to 50° C. and at times ranging from 30 minutes to 3 hours.

Alternatively one to four molar equivalents of amide anion of formula (V) can be generated from one to four molar equivalents of amide of formula (IV) in the presence of the salt of formula (III), thereupon the amide anion of formula (V) reacts with the salt of formula (III) to give the product of formula (VI). The reaction is most conveniently performed using one to ten molar equivalents of sodium hydroxide, potassium hydroxide, sodium bicarbonate, or potassium carbonate in an aqueous alcohol solvent, such as ethanol. The reaction is performed conveniently at temperatures ranging from 0° C. to 30° C. and at times ranging from 30 minutes to 3 hours.

Thereafter, the ester of formula (VI) is hydrolyzed with a hydrolyzing agent to give the corresponding product of formula (I). Generally speaking, this conversion is most conveniently performed by employing a base as the hydrolyzing agent. The hydrolysis is performed in the presence of sufficient water, followed by acidification of the reaction mixture, to yield the desired acid. However, it should be understood that the manner of hydrolysis for the process of this invention is not intended to be limited to basic hydrolysis since hydrolysis under acidic conditions and other variations, for example, treatment with lithium iodide in collidine (see L. F. Fieser and M. Fieser, "Reagents for Organic Synthesis", John Wiley and Sons, Inc., New York, 1969, pp 615–617), or treatment with iodotrimethylsilane in carbon tetrachloride, or acetonitrile (see M. E. Jung et al, J. Am. Chem. Soc., 99, 968 (1977), also are applicable. Hydrolysis under acidic conditions is preferred when the ester is a tert-butyl ester.

For basic hydrolysis, a preferred embodiment involves subjecting the ester to the action of a strong base, for example, sodium or potassium hydroxide, in the presence of sufficient water to effect hydrolysis of the ester. The hydrolysis is performed using a suitable solvent, for example, methanol, ethanol or tetrahydrofuran. The reaction mixture is maintained at a temperature of from about 25° C. to 50° C., or at the reflux temperature of the solvent employed until hydrolysis occurs. Usually from 10 minutes to 6 hours is sufficient for this hydrolysis. The reaction mixture is then rendered acidic with an acid, for example, acetic acid, hydrochloric acid or sulfuric acid to release the free acid.

The following examples further illustrate this invention.

EXAMPLE 1

N-[(Cyanoimino)[6-methoxy-5-(trifluoromethyl)-1-naphthalenyl]methyl]-N-methylglycine, Methyl Ester

[(VI): R= —CN and $R^1$= —CH$_3$]

Triethyloxonium tetrafluoroborate (1M in dichloromethane, 24 mL, 24 mmol) was added to N-[[6-methoxy-5-(trifluoromethyl)-1-naphthalenyl]thioxomethyl]-N-methylglycine, methyl ester [(II), $R^1$= —CH$_3$; 8.0 g, 21.6 mmol, described in U.S. Pat. No. 4,568,693

(Example 23)], and the solution was stirred at reflux temperature under a dry nitrogen atmosphere for four days. The reaction mixture was cooled to room temperature and the dichloromethane was removed in vacuo. The remaining brown thick oil was triturated with anhydrous diethyl ether. The ether triturate was discarded. To the remaining material, ethanol (200 mL), cyanamide [(IV), R= —CN; 3.63 g, 86.4 mmol], and saturated aqueous sodium bicarbonate were added. The pH of the reaction mixture was adjusted to 8-9 with 20% aqueous sodium hydroxide and the reaction mixture was stirred at room temperature for one hour. The ethanol was removed in vacuo and water (100 mL) was added. This aqueous emulsion was extracted with ethyl ether (4×100 mL). The combined ether extracts were dried (MgSO$_4$) and the solvent was removed in vacuo. The remaining oil was flash chromatographed (19:1 dichloromethane:acetonitrile eluent, silica gel) to give 3.49 g of product as an oil.

NMR (CDC$_3$, 200 MHz, mixture of rotamers in 3.3:1 ratio; major isomer reported first): δ 2.87, 3.37 (2s, 3H, NCH$_3$), 3.89, 3.63 (2s, 3H, CO$_2$CH$_3$), 4.02 (s, 3H, OCH$_3$), 4.06 (d, 1H, J=17 Hz, —NCH$^1$H$^2$CO$_2$CH$_3$), 4.89 (d, 1H, J=17 Hz, NCH$^1$H$^2$CO$_2$CH$_3$), 7.25–8.4(m, 5H, ArH)

IR (CHCl$_3$, cm$^{-1}$): 2200 (CN), 1745 (CO$_2$CH$_3$), 1560 (C=N)

MS: (m/e) 379 (M+, 62%), 320 (20%), 277 (100%)

EXAMPLE 2

N-[[6-Methoxy-5-(trifluoromethyl)-1-naphthalenyl][[(trifluoromethyl)sulfonyl]imino]methyl]-N-methylglycine, Methyl Ester

[(VI): R= —SO$_2$CF$_3$ and R$^1$= —CH$_3$]

Triethyloxonium tetrafluoroborate (1M in dichloromethane, 30 mL, 30 mmol) was added to (II) [R$^1$= —CH$_3$, 10.0 g, 26.95 mmol, as described in Example 1] and the solution was heated at reflux temperature under a dry nitrogen atmosphere for three days. The reaction mixture was cooled to room temperature and the solvent was removed in vacuo. The remaining tar was triturated with ether (2×30 mL). The ether triturates were discarded. This remaining tar contained the ethyl thioimidate tetrafluoroborate [(III), R$^1$= —CH$_3$)].

In a separate reaction flask, a solution of trifluoromethanesulfonamide [(IV), R= —SO$_2$CF$_3$, 4.27 g, 31.8 mmol] in anhydrous ethanol (50 mL) was added to a cold (0°–10° C.), stirred solution of potassium tert-butoxide (3.21 g, 31.8 mmol) in anhydrous ethanol (50 mL) under a dry nitrogen atmosphere. To this potassium trifluoromethane sulfonamide solution [(V), R= —SO$_2$CF$_3$] was added a solution of the previously prepared ethylthioimidate tetrafluoroborate [(III), R$^1$= —CH$_3$] in anhydrous ethanol (100 mL), over a ten minute period. The reaction mixture was warmed to room temperature and stirred for 45 minutes. The ethanol was removd in vacuo and water was added. The aqueous emulsion was extracted with ethyl acetate (2×300 mL). The solvent of the combined ethyl acetate solution was removed. The crude product was flash chromatographed (gradient elution, 7:3→1:1 petroleum ether:ethyl acetate, silica gel) to give 2.62 g of product as an off white solid, m.p. 108°–110° C.

IR (CHCl$_3$, cm$^{-1}$): 1755 (C=O), 1545 (C=N)

MS: (m/e) 486 (M+, 6%), 337 (7%), 280 (6%), 251 (93%), 221 (24%), 208 (51%), 158 (66%), 102 (100%)

Anal. Calcd.: C, 44.44%; H, 3.32%; N, 5.76%; Found: C, 44.68%; H, 3.69%; N, 5.46%.

EXAMPLE 3

N-[[(4-Bromophenyl)sulfonyl]imino][6-methoxy-5-(trifluoromethyl)-1-naphthalenyl]methyl]-N-methylglycine, Methyl Ester

[(VI): R= —SO$_{2p}$—BrC$_6$H$_4$; R$^1$= —CH$_3$]

The title compound (4.49 g, white solid) was prepared from N-[[6-methoxy-5-(trifluoromethyl)-1-naphthalenyl]thioxomethyl]-N-methylglycine, methyl ester [(II), R$^1$= —CH$_3$, 10.0 g, 26.95 mmol, as described in Example 1] by the procedure used in Example 2, and substituting 4-(bromophenyl)sulfonamide [(IV), R=SO$_{2p}$—BrC$_6$H$_4$] for trifluoromethanesulfonamide [(IV), R=SO$_2$CF$_3$], m.p. 150°–153° C.

IR (CHCl$_3$, cm.$^{-1}$): 1750 (C=O), 1530 (C=N)

MS: (m/e) 574 (4%), 572 (M+, 4%), 252 (33%), 221 (30%), 219 (22%), 102 (100%)

Anal. Calcd.: C, 48.17%; H, 3.52%; N, 4.89%; Found: C, 48.50%; H, 39.2%; N, 4.71%.

EXAMPLE 4

N-[(Cyanoimino)[6-methoxy-5-(trifluoromethyl)-1-naphthalenyl]methyl]-N-methylglycine

[(I): R= —CN]

Aqueous sodium hydroxide (10%, 3.15 mL, 8.73 mmol) was added to a stirred solution of N-[(cyanoimino)[6-methoxy-5-(trifluoromethyl)-1-naphthalenyl]methyl]-N-methylglycine, methyl ester [(VI), R= —CN, R$^1$= —CH$_3$, described in Example 1, 3.31 g, 8.73 mmol] in 1:1 THF:methanol (30 mL) at room temperature. After disappearance of starting material as indicated by thin layer chromatography (20 minutes), the reaction mixture was concentrated and water (70 mL) was added. This aqueous phase was extracted with ether to remove neutral impurities (1×80 mL). This ether extract was discarded. The aqueous phase was acidified with concentrated hydrochloric acid to pH 1-3. The aqueous acid phase was then extracted with ether (5×80 mL). The combined ether extracts were dried (MgSO$_4$) and concentrated. The crude product was triturated with anhydrous ether to provide the product as an off white solid (1.56 g), m.p. 185°–189° C. (dec).

NMR (DMSO-d$^6$, 400 MHz): δ 2.82 (s, 3H, NCH$_3$), 4.05 (s, 3H, OCH$_3$), 4.34 (d, 1H, J=17 Hz, NCH$^1$H$^2$CO$_2$H), 4.62 (d, 1H, J=17 HZ, NCH$^1$H$^2$CO$_2$H), 7.51 (d, 1H, J=7 Hz, ArH), 7.79 (m, 2H, ArH), 8.22 (m, 2H, ArH)

IR (KBr, cm$^{-1}$): 3300–2400 (CO$_2$H), 2180 (CN), 1760 and 1730 (CO$_2$H), 1560 (C=N)

MS: (m/e) 365 (M+, 13%), 322 (73%), 321 (100%), 277 (27%)

Anal. Calcd.: C, 55.89%; H, 3.86%; N, 11.50%; Found: C, 56.13%; H, 3.71%; N, 11.11%.

EXAMPLE 5

N-[[6-Methoxy-5-(trifluoromethyl)-1-naphthalenyl]-[[(trifluoromethyl)sulfonyl]imino]methyl]-N-methylglycine

[(I): R= —SO$_2$CF$_3$]

The title compound was obtained by following the procedure of Example 4, but replacing N-[(cyanoimino)[6-methoxy-5-(trifluoromethyl)-1-naphthalenyl]methyl]-N-methylglycine, methyl ester [(VI), R=—CN, $R^1$=—CN, $R^1$=—$CH_3$] with an equivalent amount of N-[[6-methoxy-5-(trifluoromethyl)-1-naphthalenyl]-[[(trifluoromethyl)sulfonyl]imino]methyl]-N-methylglycine, methyl ester [(IV), R= —$SO_2CF_3$, $R^1$= —$CH_3$, as described in Example 2]. The crude product was purified by recrystallization from benzene:acetonitrile:isopropanol, m.p. 185°–190° C. (dec).

NMR (DMSO-$d^6$, 80 MHz): δ 2.85 (s, 3H, $NCH_3$), 4.07 (s, 3H, $OCH_3$), 4.4 (d, 2H, $NCH^1H^2$), 4.85 (d, 2H, $NCH^1H^2$), 7.4–8.4 (m, 5H, ArH)

IR (KBr, $cm^{-1}$): 3650–2400 ($CO_2H$), 1750 (C=O), 1560 (C=N)

MS: (m/e) 472 ($M^+$, 9%), 104 (100%)

Anal. Calcd.: C, 43.32%; H, 2.99%; N, 5.93%; Found: C, 43.25%; H, 3.24%; N, 5.82%.

EXAMPLE 6

N-[[[(4-Bromophenyl)sulfonyl]imino][6-methoxy-5-(trifluoromethyl)-1-naphthalenyl]methyl]-N-methylglycine

[(I): R= —$SO_{2p}$—$BrC_6H_4$]

The title compound was obtained by following the procedure of Example 4, but replacing N-[(cyanoimino)[6-methoxy-5-(trifluoromethyl)-1-naphthalenyl]-methyl]-N-methylglycine, methyl ester [(VI), R= —CN, $R^1$= —$CH_3$] with an equivalent amount of N-[[[(4-bromophenyl)sulfonyl]imino][6-methoxy-5-(trifluoromethyl)-1-naphthalenyl]methyl]-N-methylglycine, methyl ester [(VI), R= —$SO_{2p}$—$BrC_6H_4$, $R^1$= —$CH_3$, as described in Example 3]. The crude product was purified by recrystallization from benzene acetonitrile, m.p. 208°–212° C. (dec.).

NMR (DMSO-$d^6$, 80 MHz): δ 2.69 (s, 3H, $NCH_3$), 4.03 (s, 3H, $OCH_3$), 4.30 (d, 1H, $NCH^1H^2$), 4.70 (d, 1H, $NCH^1H^2$), 7.0–8.40 (m, 9H, ArH)

IR (KBr, $cm^{-1}$): 3650–2400 ($CO_2H$), 1745 (C=O), 1540 (C=N)

MS: (CI) 561 (30%), 559 (M+1, 28%), 543 (10%), 541 (10%), 342 (100%)

Anal. Calcd.: C, 47.23%; H, 3.25%; N, 5.01%; Found: C, 47.18%; H, 3.55%; N, 4.98%

We claim:

1. The process for the production of compounds of formula (I)

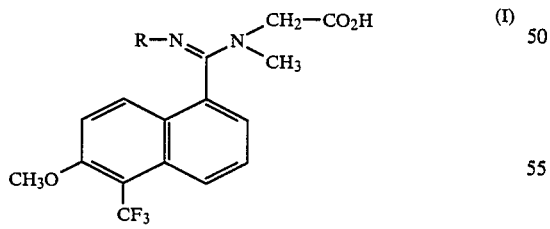

wherein R is —CN, —$SO_2CF_3$, or —$SO_{2p}$—$BrC_6H_4$ which comprises (a) reacting a thioamidoester of formula (II)

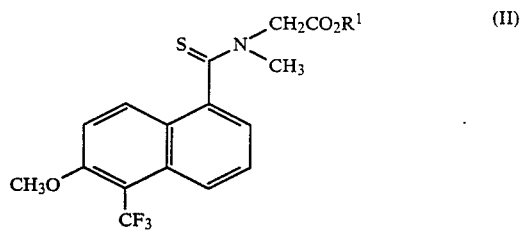

wherein $R^1$ is lower alkyl or Ar(lower) alkyl with triethyloxonium tetrafluoroborate to give the corresponding ethylthioimidate tetrafluoroborate salt of formula (III)

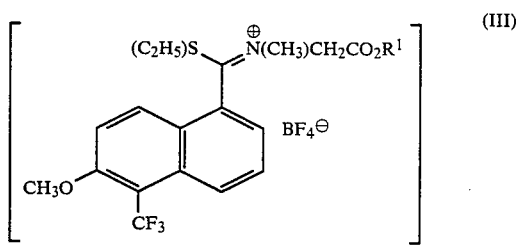

wherein $R^1$ is defined as above;

(b) reacting an amide of formula (IV)

R—$NH_2$       (IV)

wherein R is —CN, —$SO_2CF_3$, or —$SO_{2p}$—$BrC_6H_4$ with a base to give the corresponding amide anion of formula (V)

[R—$N^{\ominus}H$]     (V)

wherein R is defined as above;

(c) reacting the salt of formula (III) wherein $R^1$ is defined as above with the amide anion of formula (V) wherein R is defined as above to give corresponding amidine ester of formula (VI)

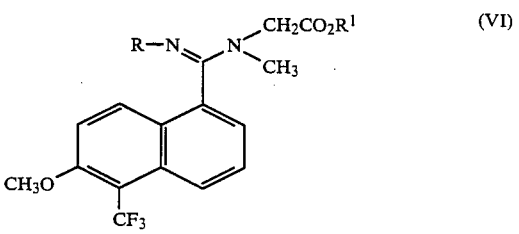

wherein R and $R^1$ are defined as above.

* * * * *